United States Patent
Tidow et al.

(10) Patent No.: US 7,194,964 B2
(45) Date of Patent: Mar. 27, 2007

(54) METHOD FOR CHEMICALLY DECONTAMINATING SOIL BY APPLYING A MIXTURE OF SULPHUR AND COMPLEXING AGENTS

(75) Inventors: Jörn Tidow, Schwetzingen (DE); Herbert Scholz, Neustadt (DE); Adolf Parg, Bad Dürkheim (DE); Reinhold Stadler, Kirrweiler (DE); Karl-Heinrich Schneider, Kleinkarlbach (DE); Reinhardt Hähndel, Limburgerhof (DE); Gerhard Pompejus, Neustadt (DE); Francesc Riera Forcades, Barcelona (ES)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/512,420

(22) PCT Filed: Apr. 16, 2003

(86) PCT No.: PCT/EP03/03972

§ 371 (c)(1),
(2), (4) Date: Jun. 8, 2005

(87) PCT Pub. No.: WO03/090541

PCT Pub. Date: Nov. 6, 2003

(65) Prior Publication Data

US 2005/0226902 A1 Oct. 13, 2005

(30) Foreign Application Priority Data

Apr. 23, 2002 (DE) .................... 102 18 162

(51) Int. Cl.
*A01C 23/00* (2006.01)

(52) U.S. Cl. .............. 111/118; 111/200; 111/900; 504/162; 504/349

(58) Field of Classification Search ............ 111/118, 111/900, 200; 504/116.1, 117, 162, 349, 504/350
See application file for complete search history.

(56) References Cited

U.S. PATENT DOCUMENTS 2,957,798 A  10/1960  Hennicke

FOREIGN PATENT DOCUMENTS

EP  1 293 125  3/1993

OTHER PUBLICATIONS

Derwent Abst. 87-123845/18= EP 220 655.
Database Biosis Online, Biosciences Information Service, Philadelphia, PA, U.S. 1993, Powell NL: "Spray-tank-mix compatibility of magnese, boron and fungicide: Solution pH and precipitation" (XP-002245373).
Rudolf Heitefuss, "Pflanzenschutz", 3. Auflae, Georg Thieme Verlag Stuttgard, New York, 200 Seiten 227 bis 229.
CIPAC Handbook F—p. 420—Dry Sieve Analysis of Waterdispersible Granules.
Arid zone irrigation 1973, Springer Verlag; Kapitel "Irrigation Technology", pp. 303-353.
Roempp Chemielexikon, 9. Auflage, Band 3, Georg-Thieme Verlag, Stuttgard, New York 1990, Seite 2511.
Derwent Abst. DE 26 04 695.
Derwent Abst. FR 2599-592.

*Primary Examiner*—Christopher J. Novosad
(74) *Attorney, Agent, or Firm*—Novak Druce & Quigg LLP

(57) ABSTRACT

In a chemical soil disinfestation method, a fungicidally, insecticidally or nematicidally active amount of a mixture M comprising a component a) of a1) 20 to 96% by weight of sulfur, a2) 4 to 80% by weight of a complexing agent and, if appropriate, one or more crop protection agents b) and/or additives c) is applied.

9 Claims, No Drawings

METHOD FOR CHEMICALLY DECONTAMINATING SOIL BY APPLYING A MIXTURE OF SULPHUR AND COMPLEXING AGENTS

The present invention relates to chemical soil disinfestation methods in which a fungicidally, insecticidally or nematicidally active amount of a mixture M comprising a component a) of a1) 20 to 96% by weight of sulfur, a2) 4 to 80% by weight of a complexing agent and, if appropriate, one or more crop protection agents b) and/or further additives c) is applied and to the use of a mixture M as chemical soil disinfestation composition.

Mixtures of elemental sulfur and various auxiliaries are known in the agricultural sector as fungicides and/or acaricides and commercially available for example in the form of the product KUMULUS® from BASF Aktiengesellschaft. The plants to be treated are generally wetted with compositions comprising the elemental sulfur, for example by directly dusting the plants.

In contrast, the use of mixtures of elemental sulfur and complexing agent for chemically disinfesting the soil is not known. Toxically and ecologically unacceptable chemicals, whose use has been greatly restricted in recent years, have been employed for this purpose (Rudolf Heitefuss, "Pflanzenschutz" [Crop protection], 3rd Edition, Georg Thieme Verlag Stuttgart, New York, 2000, pages 227 to 229).

A system widely used for irrigating crops, for example useful plants and/or ornamentals, is what is known as the trickle irrigation system, where nozzles, which are fed by a tank via a pipeline, spray the nutrients and/or crop protectants, in general in aqueous solution, dispersion or suspension, into the vicinity of the roots of the plants. The nutrients and/or crop protectants are advantageously premixed in a storage tank which feeds the pipeline or the spray nozzles. In this method, the leaves of the crop plants do not come into contact with the solution of nutrients and/or crop protectants.

It is an object of the present invention to develop a method or a product by means of which chemical soil disinfestation is made possible, but where the composition to be employed is toxicologically and ecologically largely acceptable and can be handled with ease.

It has been found that this object is achieved by a chemical soil disinfestation method in which a fungicidally, insecticidally or nematicidally active amount of a mixture M comprising a component a) of a1) 20 to 96% by weight of sulfur, a2) 4 to 80% by weight of a complexing agent and, if appropriate, one or more crop protection agents b) and/or further components c) is applied and the use of a mixture M as soil disinfestation composition.

The nature of the sulfur present in the mixture according to the invention is not critical. Any elemental sulfur which has been known for a long time, has been described extensively and is commercially available may be used. A product which is highly suitable is, for example, the sulfur which can be obtained from natural-gas cleaning plants.

The amount of the sulfur a1) in component a) according to the invention is in the range of from 20 to 96% by weight, preferably 70 to 95% by weight and in particular 75 to 85% by weight, in each case based on the total weight of component a).

Substances which are suitable as complexing agent a2) are nonpolymeric sequestrants, but preferably polymeric sequestrants. The complexing agent a2) may comprise the pure sequestrants or else any mixtures of the pure sequestrants, the mixing ratio not being critical.

Substances which are suitable as nonpolymeric sequestrants are EDTA (ethylenediaminetetraacetic acid), NTA (nitrilotriacetic acid), EDDHA (ethylenediaminedi(ortho-hydroxyphenyl)acetic acid), DTPA (diethylenetriaminepentaacetic acid), HEDTA (hydroxyethylenediaminetriacetic acid), preferably ethylenediaminetetraacetic acid and/or diethylenetriaminepentaacetic acid.

Substances which are suitable as polymeric sequestrants are polyacrylic acid and its salts, in particular the sodium salts, polymethacrylic acid and its salts, in particular the sodium salts, polymaleic acid, prepared for example by hydrolyzing polymaleic anhydride, in particular the sodium salts, polyvinylpyrrolidone, acrylic acid/maleic acid copolymers, in particular the sodium salts, vinylpyrrolidone/vinyl acetate copolymers, vinylpyrrolidone and $C_{20}$-α-olefin graft copolymers, vinylpyrrolidone/acrylic acid copolymers, vinylpyrrolidone/dimethylaminoethyl acrylate copolymers, copolymers of methyl vinyl ether and maleic acid anhydride (derivatives), styrene/maleic anhydride copolymers, polyaspartic acid and its salts, poly-p-vinylbenzenesulfonic acid and its salts, copolymers of ethylene and/or propylene and/or isobutene and (meth)acrylic acid, modified starches, modified celluloses, for example carboxymethylcellulose, alginates, lignin derivatives such as lignosulfonates, chitosans, modified polysaccharides, phenolsulfonic acid/formaldehyde condensates, and naphthalenesulfonic acid/formaldehyde condensates.

The following are preferably used as polymeric sequestrants a2): lignosulfonates, naphthalenesulfonic acid/formaldehyde condensates, polyacrylic acid and its salts, in particular the sodium salts, polymethacrylic acid and its salts, in particular sodium salts, polymaleic acid or its salts, prepared for example by hydrolyzing polymaleic anhydride, in particular the sodium salts, acrylic acid/maleic acid copolymers, in particular the sodium salts, polyacrylates, polyaspartates and other polyamino acids. Polymeric sequestrants which are used in particular are lignosulfonates and/or naphthalenesulfonic acid/formaldehyde condensates.

Lignosulfonates are known and are defined, for example, in Römpp Chemilexikon [Römpp's dictionary of chemistry], 9th Edition, volume 3, Georg-Thieme Verlag, Stuttgart, New York 1990, page 2511. Lignosulfonates which are highly suitable are the alkali metal salts and/or alkaline earth metal salts and/or ammonium salts, for example the ammonium, sodium, potassium, calcium or magnesium salts of lignosulfonic acid. The sodium, potassium or calcium salts are preferably used, the sodium, potassium and/or calcium salts are very particularly preferably used.

Naturally, the term lignosulfonates also encompasses mixed salts of different ions, such as potassium/sodium lignosulfonate, potassium/calcium lignosulfonate and the like, in particular sodium/calcium lignosulfonate.

Naphthalenesulfonic acid/formaldehyde condensates are likewise known and commercially available for example in the form of Tamol® products from BASF Aktiengesellschaft.

The amount of the sequestrant a2) in component a) according to the invention is in the range of from 4 to 80% by weight, preferably 5 to 30% by weight and in particular 15 to 25% by weight, in each case based on the total weight of component a).

If a mixture of lignosulfonate and naphthalenesulfonic acid/formaldehyde condensate is used as component a2), the lignosulfonate usually amounts to in the range of from 10 to 90% by weight in this mixture and the naphthalenesulfonic acid/formaldehyde condensate forms the complement of in the range of from 90 to 10% by weight in this mixture.

Components a) according to the invention which are particularly suitable are those consisting of 75 to 85% by weight of sulfur and 15 to 25% by weight of lignosulfonate.

Examples of components a) according to the invention are: 95% by weight of sulfur+5% by weight of sodium lignosulfonate; 90% by weight of sulfur+10% by weight of sodium lignosulfonate; 80% by weight of sulfur+20% by weight of sodium lignosulfonate; 75% by weight of sulfur+25% by weight of sodium lignosulfonate; 75% by weight of sulfur+25% by weight of potassium lignosulfonate, 95% by weight of sulfur+5% by weight of potassium lignosulfonate; 90% by weight of sulfur+10% by weight of potassium lignosulfonate; 80% by weight of sulfur+20% by weight of potassium lignosulfonate; 95% by weight of sulfur+5% by weight of calcium lignosulfonate; 90% by weight of sulfur+10% by weight of calcium lignosulfonate; 80% by weight of sulfur+20% by weight of calcium lignosulfonate.

The mixture M according to the invention, or component a), can be prepared by mixing, comminuting, drying, for example spray-drying.

As a rule, the mixture M according to the invention, or component a), is in the form of free-flowing granular particles with a mean particle size—Dry Sieve Analysis of Waterdispersible Granules as specified in CIPAC MT 170, CIPAC Handbook F—Page 420—in the range of from 50 µm to 4 mm, preferably in the range of from 100 µm to 2 mm, whose primary particles are, as a rule, 0.05 to 8 µm in size (as determined by Particle Size Analysis—Laser Diffraction Methods, ISO 13320-1:1999).

In addition to component a), the mixture M according to the invention may additionally comprise one or more crop protection agents b) and/or further components c).

Suitable crop protection agents b) are herbicides, pesticides and fungicides. Pesticides are understood as meaning, inter alia, acaricides, insecticides and nematicides.

Preferred herbicides, fungicides, acaricides, insecticides and nematicides are disclosed in http://www.hclrss.demon.co.uk/index_cn_frame.html (Index of common names). A list of preferred herbicides, fungicides, acaridices, insecticides and nematicides is disclosed hereinbelow, some of the active ingredients being mentioned several times with different "common names": abamectin; acephate; acequinocyl; acetamiprid; acethion; acetochlor; acetoprole; acifluorfen; aclonifen; ACN; acrinathrin; acrolein; acrylonitrile; acypetacs; alachlor; alanap; alanycarb aldicarb; aldimorph; aldoxycarb; aldrin; allethrin; d-trans-allethrin; allidochlor; allosamidin; alloxydim; allyl alcohol; allyxycarb; alorac; alpha-cypermethrin; ametridione; ametryn; ametryne; amibuzin; amicarbazone; amidithion; amidoflumet; amidosulfuron; aminocarb; aminotriazole; amiprofos-methyl; amiton; amitraz; amitrole; ammonium sulfamate; ampropylfos; AMS; anabasine; anilazine; anilofos; anisuron; arprocarb; arsenous oxide; asulam; athidathion; atraton; atrazine; aureofungin; avermectin B1; azaconazole; azadirachtin; azafenidin; azamethiphos; azidithion; azimsulfuron; azinphos-ethyl (=azinphosethyl); azinphos-methyl (=azinphosmethyl); aziprotryn (=aziprotryne); azithiram; azobenzene; azocyclotin; azothoate; azoxystrobin; barban (=barbanate); barium hexafluorosilicate; barium polysulfide; barium silicofluoride; barthrin; BCPC; beflubutamid; benalaxyl; benazolin; bendiocarb; bendioxide; benefin (=benfluralin); benfuracarb; benfuresate; benodanil; benomyl; benoxafos; benquinox; bensulfuron; bensulide; bensultap; bentaluron; bentazon (=bentazone); benthiocarb; benzadox; benzalkonium chloride; benzamacril; benzamizole; benzamorf; benzene hexachloride; benzfendizone; benzipram; benzobicyclon; benzoepin; benzofenap; benzofluor; benzohydroxamic acid; benzomate benzoximate (=benzoylprop); benzthiazuron; benzyl benzoate; beta-cyfluthrin; beta-cypermethrin; bethoxazin; BHC; gamma-BHC; bialaphos; bifenazate; bifenox; bifenthrin; bilanafos; binapacryl; bioallethrin; bioethanomethrin; biopermethrin; bioresmethrin; biphenyl; bispyribac; bistrifluron; bitertanol; bithionol; blasticidin-S; borax; Bordeaux mixture; BPPS; bromacil; bromchlophos; bromfenvinfos; bromobonil; bromobutide; bromocyclen; bromo-DDT; bromofenoxim; bromomethane; bromophos; bromophos-ethyl; bromopropylate; bromoxynil; brompyrazon; bromuconazole; BRP; bufencarb; bupirimate; buprofezin; Burgundy mixture; butacarb; butachlor; butafenacil; butam; butamifos; butathiofos; butenachlor; buthidazole; buthiobate; buthiuron; butocarboxim; butonate; butoxycarboxim; butralin; butroxydim; buturon; butylamine; butylate; butylchlorophos; cacodylic acid; cadusafos; cafenstrole; calcium arsenate; calcium chlorate; calcium cyanamide; calcium polysulfide; cambendichlor; camphechlor; captafol; captan; carbam; carbamorph; carbanolate; carbaryl; carbasulam; carbathion; carbendazim; carbetamide; carbofuran; carbon disulfide; carbon tetrachloride; carbophenothion; carbophos; carbosulfan; carboxazole; carboxin; carfentrazone; carpropamid; cartap; carvone; CDAA; CDEA; CDEC; CEPC; cerenox; cevadilla; Cheshunt mixture; chinalphos; chinalphos-méthyl; chinomethionat; chlobenthiazone; chlomethoxyfen; chlor-IPC; chloramben; chloraniformethan; chloranil; chloranocryl; chlorazifop; chlorazine; chlorbenside; chlorbicyclen; chlorbromuron; chlorbufam; chlordane; chlordecone; chlordimeform; chlorethoxyfos; chloreturon; chlorfenac; chlorfenapyr; chlorfenazole; chlorfenethol; chlorfenidim; chlorfénizon; chlorfenprop; chlorfenson; chlorfensulphide; chlorfenvinphos; chlorfenvinphos-methyl; chlorfluazuron; chlorflurazole; chlorflurecol; chlorflurenol; chloridazon; chlorimuron; chlorinate; chlormephos; chlormethoxynil; chlornitrofen; chloroacetic acid; chlorobenzilate; chloroform; chloromebuform; chloromethiuron; chloroneb; chlorophos; chloropicrin; chloropon; chloropropylate; chlorothalonil; chlorotoluron; chloroxifenidim (=chloroxuron); chloroxynil; chlorphoxim; chlorprazophos; chlorprocarb; chlorpropham; chlorpyrifos; chlorpyrifos-methyl; chlorquinox; chlorsulfuron; chlorthal; chlorthiamid; chlorthiophos; chlortoluron; chlozolinate; chromafenozide; cinerin I; cinerin II; cinidonethyl, cinmethylin; cinosulfuron; cisanilide; cismethrin; clethodim; climbazole; cliodinate; clodinafop; cloethocarb; clofentezine; clofop; clomazone; clomeprop; cloprop; cloproxydim; clopyralid; cloransulam; closantel; clothianidin; clotrimazole; CMA; CMMP; CMP; CMU; copper acetate; copper acetoarsenite; copper arsenate; copper carbonate, basic; copper hydroxide; copper naphthenate; copper oleate; copper oxychloride; copper 8-quinolinolate; copper silicate; copper sulfate; copper sulfate, basic; copper zinc chromate; coumaphos; coumithoate; 4-CPA; 4-CPB; CPMF; 4-CPP; CPPC; cresol (=cresylic acid); crotamiton; crotoxyfos (=crotoxyphos); crufomate; cryolite; cufraneb; cumyluron; cuprobam; cuprous oxide; CVMP; cyanatryn; cyanazine; cyanofenphos; cyanophos; cyanthoate; cyazofamid; cyclafuramid; cyclethrin; cycloate; cycloheximide; cycloprothrin; cyclosulfamuron; cycloxydim; cyflufenamid; cycluron; cyfluthrin; beta-cyfluthrin; cyhalofop; cyhalothrin; gamma-cyhalothrin; lambda-cyhalothrin; cyhexatin; cymoxanil; cypendazole; cypermethrin; alpha-cypermethrin; beta-cypermethrin; theta-cypermethrin; zeta-cypermethrin; cyperquat; cyphenothrin; cyprazine; cyprazole; cyprex; cyproconazole; cyprodinil; cyprofuram; cypromid; cyromazine; cythioate; 2,4-D; 3,4-DA; daimuron; dalapon; dazomet; 2,4-DB; 3,4-DB; DBCP; DCB; DCIP; DCPA (USA); DCPA (Japan); DCU; DDD; DDPP; DDT; pp (pure)-DDT; DDVP; 2,4-DEB; debacarb; decafentin; decarbofuran; dehydroacetic acid; deiquat; delachlor; delnav; deltamethrin; demephion; demephion-O; demephion-S; demeton; demeton-methyl; demeton-O; demeton-O-methyl; demeton-S; demeton-S-methyl; demeton-S-methylsulphon (=demeton-S-methyl sulphone); DEP; 2,4-DEP; depalléthrine; derris; 2,4-DES; desmedipham; desmetryn (=desmetryne); diafenthiuron; dialifor (=dialifos); di-allate (=diallate); diamidafos; dianat; diazinon; dibrom; 1,2-dibromoethane; dicamba; dicapthon; dichlobenil; dichlofenthion; dichlofluanid; dichlone; dichloralurea; dichlorfenidim; dichlormate; o-dichlorobenzene (=ortho-dichlorobenzene); p-dichlorobenzene (=para-dichlorobenzene); 1,2-dichloroethane; dichloromethane; dichlorophen; 1,2-dichloropropane; 1,3-dichloropropene; dichlorprop; dichlorprop-P; dichlorvos; dichlozoline; diclobutrazol; diclocymet; diclofop; diclomezine; dicloran; diclosulam; dicofol; dicresyl; dicrotophos; dicryl; dicyclanil; dieldrin; dienochlor; diethamquat; diethatyl; diethion (=diéthion); diethofencarb; diethyl pyrocarbonate; difenoconazole; difenopenten; difenoxuron; difenzoquat; diflubenzuron; diflufenican (=diflufenicanil); diflufenzopyr; diflumetorim; dilor; dimefox; dimefuron; dimehypo; dimepiperate; dimetan; dimethachlor; dimethametryn; dimethenamid; dimethenamid-P; dimethirimol; dimethoate; dimethomorph; dimethrin; dimethylvinphos; dimetilan; dimexano; dimidazon; dimoxystrobin; dimpylate; dinex; diniconazole; diniconazole-M; dinitramine; dinobuton; dinocap; dinocap-4; dinocap-6; dinocton; dinofenate; dinopenton; dinoprop; dinosam; dinoseb; dinosulfon; dinotefuran; dinoterb; dinoterbon; diofenolan; dioxabenzofos; dioxacarb; dioxathion; diphenamid; diphenyl sulfone; diphenylamine; diphenylsulphide; dipropetryn; dipterex; dipyrithione; diquat; disugran; disul; disulfiram; disulfoton; ditalimfos; dithianon; dithicrofos; dithiométon; dithiopyr; diuron; dixanthogen; DMPA; DNOC; dodemorph; dodicin; dodine; dofenapyn; doguadine; doramectin (=2,4-DP); 3,4-DP; DPC; drazoxolon; DSMA; d-trans-allethrin; dymron; EBEP; ecdysone; ecdysterone; echlomezol; EDB; EDC; EDDP (=edifenphos); eglinazine; emamectin; EMPC; empenthrin; endosulfan; endothal (=endothall); endothion; endrin; ephirsulfonate; EPN; epofenonane; epoxiconazole; eprinomectin; epronaz; EPTC; erbon; esfenvalerate; ESP; esprocarb; etaconazole; etaphos; etem; ethaboxam; ethalfluralin; ethametsulfuron; ethidimuron; ethiofencarb; ethiolate; ethion; ethiprole; ethirimol; ethoate-methyl; ethofumesate; ethoprop (=ethoprophos); ethoxyfen; ethoxyquin; ethoxysulfuron; ethyl pyrophosphate; ethylan (=ethyl-DDD); ethylene dibromide; ethylene dichloride; ethylene oxide; ethyl formate; ethylmercury acetate; ethylmercury bromide; ethylmercury chloride; ethylmercury phosphate; etinofen; ETM; etnipromid; etobenzanid; etofenprox; etoxazole; etridiazole; etrimfos; EXD; famoxadone; famphur; fenac; fenamidone; fenaminosulf; fenamiphos; fenapanil; fenarimol; fenasulam; fenazaflor; fenazaquin; fenbuconazole; fenbutatin oxide; fenchlorphos; fenethacarb; fenfluthrin; fenfuram; fenhexamid; fenidin; fenitropan; fenitrothion; fenizon; fenobucarb; fenolovo; fenoprop; fenothiocarb; fenoxacrim; fenoxanil; fenoxaprop; fenoxaprop-P; fenoxycarb; fenpiclonil; fenpirithrin; fenpropathrin; fenpropidin; fenpropimorph; fenpyroximate; fenridazon; fenson; fensulfothion; fenteracol; fenthiaprop; fenthion; fenthion-ethyl; fentiaprop; fentin; fentrazamide; fentrifanil; fenuron; fenvalerate; ferbam; ferimzone; ferrous sulfate; fipronil; flampflop; flamprop-M; flazasulfuron; flonicamid; florasulam; fluacrypyrim; fluazifop; fluazifop-P; fluazinam; fluazolate; fluazuron; flubenzimine; flucarbazone; fluchloralin; flucofuron; flucycloxuron; flucythrinate; fludioxonil; fluenetil; flufenacet; flufenerim; flufenican; flufenoxuron; flufenprox; flufenpyr; flumethrin; flumetover; flumetsulam; flumezin; flumiclorac; flumioxazin; flumipropyn; fluometuron; fluorbenside; fluoridamid; fluorochloridone; fluorodifen; fluoroglycofen; fluoroimide; fluoromidine; fluoronitrofen; fluothiuron; fluotrimazole; flupoxam; flupropacil; flupropanate; flupyrsulfuron; fluquinconazole; fluridone; flurochloridone; fluromidine; fluroxypyr; flurtamone; flusilazole; flusulfamide; fluthiacet; flutolanil; flutriafol; fluvalinate; tau-fluvalinate; folpel (=folpet); fomesafen; fonofos; foramsulforon; formaldehyde; formetanate; formothion; formparanate; fosamine; fosetyl; fosmethilan; fospirate; fosthiazate; fosthietan; fthalide; fuberidazole; furalaxyl; furametpyr; furathiocarb; furcarbanil; furconazole; furconazole-cis; furethrin; furmecyclox; furophanate; furyloxyfen; ganmma-BHC; gamma-cyhalothrin; gamma-HCH; glufosinate; glyodin; glyphosate; griseofulvin; guanoctine (=guazatine); halacrinate; halfenprox; halofenozide; halosafen; halosulfuron; haloxydine; haloxyfop; HCA; HCH; gamma-HCH; HEOD; heptachlor; heptenophos; heterophos; hexachlor (=hexachloran); hexachloroacetone; hexachlorobenzene; hexachlorobutadiene; hexaconazole; hexaflumuron; hexafluoramin; hexaflurate; hexazinone; hexylthiofos; hexythiazox; HHDN; hydramethylnon; hydrogen; cyanide; hydroprene; hydroxyisoxazole; 8-hydroxyquinoline; sulfate; hymexazol; hyquincarb; IBP; imazalil; imazamethabenz; imazamox; imazapic; imazapyr; imazaquin; imazethapyr; imazosulfuron; imibenconazole; imidacloprid; iminoctadine; imiprothrin; indanofan; indoxacarb; iodobonil; iodofenphos; iodosulfuron; ioxynil; ipazine; IPC; ipconazole; iprobenfos; iprodione; iprovalicarb; iprymidam; IPSP; IPX; isamidofos; isazofos; isobenzan; isocarbamid; isocil; isodrin; isofenphos; isomethiozin; isonoruron; isopolinate; isoprocarb; isoprocil; isopropalin; isoprothiolane; isoproturon; isothioate; isouron; isovaledione; isoxaben; isoxachlortole; isoxaflutole; isoxapyrifop; isoxathion; isuron; ivermectin; jasmolin I; jasmolin II; jodfenphos; juvenile; hormone I; juvenile; hormone II; juvenile; hormone III; karbutilate; kasugamycin; kelevan; kinoprene; kresoximmethyl; lactofen; lambda-cyhalothrin; lead arsenate; lenacil; leptophos; lime sulfur; d-limonene; lindane; linuron; lirimfos; lufenuron; lythidathion; M-74; M-81; MAA; malathion; maldison; malonoben; MAMA; mancopper; mancozeb; maneb; mazidox; MCC; MCPA; MCPA-thioethyl; MCPB; 2,4-MCPB; mebenil; mecarbam; mecarbinzid; mecarphon; mecoprop; mecoprop-P; medinoterb; mefenacet; mefluidide; menazon; MEP; mepanipyrim; mephosfolan; mepronil; mercaptodimethur; mercaptophos; mercaptophos-teolovy; mercaptothion; mercuric; chloride; mercuric oxide; mercurous; chloride; mesoprazine; mesosulfuron; mesotrione; mesulfen; mesulfenfos; mesulphen; metalaxyl; metalaxyl-M; metam; metamitron; metaphos; metaxon; metazachlor; metazoxolon; metconazole; metflurazon; methabenzthiazuron; methacrifos; methalpropalin; metham; methamidophos; methasulfocarb; methazole; methfuroxam; methibenzuron; methidathion; methiobencarb; methiocarb; methiuron; methocrotophos; métholcarb; methometon; methomyl; methoprene; methoprotryn; methoprotryne; methoxychlor; 2-methoxyethylmercury; chloride; methoxyfenozide; methyl bromide; methylchloroform; methyldithiocarbamic; acid; methyldymron; methylene; chloride; methyl; isothiocyanate; methyl-mercaptophos; methylmercaptophos; oxide; methyl-mercaptophos-teolovy; methylmercury; benzoate; methylmercury; dicyandiamide; methyl parathion; methyltriazothion; metiram; metobenzuron; metobromuron; metolachlor; S-metolachlor; metolcarb; metominostrobin; metosulam; metoxadiazone; metoxuron; metrafenone;

metribuzin; metriphonate; metsulfovax; metsulfuron; mevinphos; mexacarbate; milbemectin; milneb; mipafox; MIPC; mirex; MNAF; molinate; monalide; monisouron; monochloroacetic; acid; monocrotophos; monolinuron; monosulfiram; monuron; morfamquat; morphothion; MPMC; MSMA; MTMC; myclobutanil; myclozolin; nabam; naftalofos; naled; naphthalene; naphthalic; anhydride; naphthalophos; naproanilide; napropamide; naptalam; natamycin; neburea; neburon; nendrin; nichlorfos; niclofen; niclosamide; nicobifen; nicosulfuron; nicotine; nifluridide; nikkomycins; NIP; nipyraclofen; nitenpyram; nithiazine; nitralin; nitrapyrin; nitrilacarb; nitrofen; nitrofluorfen; nitrostyrene; nitrothal-isopropyl; nobormide; norbormide; norea; norflurazon; noruron; novaluron; noviflumuron; NPA; nuarimol; OCH; octhilinone; o-dichlorobenzene; ofurace; omethoate; orbencarb; orthobencarb; ortho-dichlorobenzene; oryzalin; ovatron; ovex; oxadiargyl; oxadiazon; oxadixyl; oxamyl; oxapyrazon; oxasulfuron; oxaziclomefone; oxine-copper; oxine-Cu; oxpoconazole; oxycarboxin; oxydemeton-methyl; oxydeprofos; oxydisulfoton; oxyfluorfen; oxythioquinox; PAC; palléthrine; PAP; para-dichlorobenzene; parafluron; paraquat; parathion; parathion-methyl; Paris green; PCNB; PCP; p-dichlorobenzene; pebulate; pédinex; pefurazoate; penconazole; pencycuron; pendimethalin; penfluron; penoxsulam; pentachlorophenol; pentanochlor; pentoxazone; perfluidone; permethrin; pethoxamid; PHC; phénétacarbe; phenisopham; phenkapton; phenmedipham; phenmedipham-ethyl; phenobenzuron; phenothiol; phenothrin; phenthoate; phenylmercuriurea; phenylmercury acetate; phenylmercury chloride; phenylmercury nitrate; phenylmercury salicylate; 2-phenylphenol; phorate; phosalone; phosdiphen; phosfolan; phosmet; phosnichlor; phosphamide; phosphamidon; phosphine; phosphocarb; phoxim; phoxim-methyl; phthalide; phthalophos; phthalthrin; picloram; picolinafen; picoxystrobin; piperophos; pirimetaphos; pirimicarb; pirimiphos-ethyl; pirimiphos-methyl; PMA; PMP; polycarbamate; polychlorcamphene; polyethoxyquinoline; polyoxins; polyoxorim; potassium arsenite; potassium cyanate; potassium polysulfide; potassium thiocyanate; pp-DDT (pure); prallethrin; precocene I; precocene II; precocene III; pretilachlor; primidophos; primisulfuron; probenazole; prochloraz; proclonol; procyazine; procymidone; prodiamine; profenofos; profluazol; profluralin; profoxydim; proglinazine; promacyl; promecarb; prometon; prometryn; prometryne; pronamide; propachlor; propafos; propamocarb; propanil; propaphos; propaquizafop; propargite; propazine; propetamphos; propham; propiconazole; propineb; propisochlor; propoxur; propoxycarbazone; propyzamide; prosulfalin; prosulfocarb; prosulfuron; prothidathion; prothiocarb; prothiofos; prothoate; protrifenbute; proxan; prymidophos; prynachlor; pydanon; pyracarbolid; pyraclofos; pyraclonil; pyraclostrobin; pyraflufen; pyrazolate; pyrazolynate; pyrazon; pyrazophos; pyrazosulfuron; pyrazoxyfen; pyresmethrin; pyrethrin I; pyrethrin II; pyrethrins; pyribenzoxim; pyributicarb; pyriclor; pyridaben; pyridafol; pyridaphenthion; pyridate; pyridinitril; pyrifenox; pyriftalid; pyrimétaphos; pyrimethanil; pyrimicarbe; pyrimidifen; pyrimitate; pyriminobac; pyrimiphos-éthyl; pyrimiphos-méthyl; pyriproxyfen; pyrithiobac; pyroquilon; pyroxychlor; pyroxyfur; quassia; quinacetol; quinalphos; quinalphos-methyl; quinazamid; quinclorac; quinconazole; quinmerac; quinoclamine; quinomethionate; quinonamid; quinothion; quinoxyfen; quintiofos; quintozene; quizalofop; quizalofop-P; rabenzazole; rafoxanide; reglone; resmethrin; rhodethanil; rimsulfuron; rodéthanil; ronnel; rotenone; ryania; sabadilla; salicylanilide; schradan; sebuthylazine; secbumeton; selamectin; sesone; sethoxydim; sevin; siduron; silafluofen; silthiofam; silvex; simazine; simeconazole; simeton; simetryn; simetryne; SMA; sodium arsenite; sodium chlorate; sodium fluoride; sodium hexafluorosilicate; sodium orthophenylphenoxide; sodium pentachlorophenate; sodium pentachlorophenoxide; sodium o-phenylphenoxide; sodium polysulfide; sodium silicofluoride; disodium tetraborate; sodium thiocyanate; solan; sophamide; spinosad; spirodiclofen; spiroxamine; stirofos; streptomycin; sulcofuron; sulcotrione; sulfallate; sulfentrazone; sulfiram; sulfluramid; sulfometuron; sulfosulfuron; sulfotep; sulfotepp; sulfur; sulfuric acid; sulfuryl fluoride; sulglycapin; sulprofos; sultropen; swep; 2,4,5-T; tau-fluvalinate; tazimcarb; 2,4,5-TB; 2,3,6-TBA; TBTO; TBZ; TCA; TCBA; TCMTB; TCNB; TDE; tebuconazole; tebufenozide; tebufenpyrad; tebupirimfos; tebutam; tebuthiuron; tecloftalam; tecnazene; tecoram; tedion; teflubenzuron; tefluthrin; temephos; TEPP; tepraloxydim; terallethrin; terbacil; terbucarb; terbuchlor; terbufos; terbumeton; terbuthylazine; terbutol; terbutryn; terbutryne; terraclor; tetrachloroethane; tetrachlorvinphos; tetraconazole; tetradifon; tetradisul; tetrafluron; tetramethrin; tetranactin; tetrasul; thenylchlor; theta-cypermethrin; thiabendazole; thiacloprid; thiadiazine; thiadifluor; thiamethoxam; thiameturon; thiazafluron; thiazone; thiazopyr; thicrofos; thicyofen; thidiazimin; thidiazuron; thifensulfuron; thifluzamide; thiobencarb; thiocarboxime; thiochlorfenphim; thiochlorphenphime; thiocyclam; thiodan; thiodicarb; thiofanocarb; thiofanox; thiomersal; thiometon; thionazin; thiophanate; thiophanate-ethyl; thiophanate-methyl; thiophos; thioquinox; thiosultap; thiram; thiuram; thuringiensin; tiabendazole; tiocarbazil; tioclorim; tioxymid; TMTD; tolclofos-methyl; tolylfluanid; tolfenpyrad; tolylmercury acetate; toxaphene; 2,4,5-TP; 2,3,3-TPA; TPN; tralkoxydim; tralomethrin; d-trans-allethrin; transfluthrin; transpermethrin; tri-allate; triadimefon; triadimenol; triallate; triamiphos; triarathene; triarimol; triasulfuron; triazamate; triazbutil; triaziflam; triazophos; triazothion; triazoxide; tribenuron; tributyltin oxide; tricamba; trichlamide; trichlorfon; trichlormetaphos-3; trichloronat; trichloronate; trichlorphon; triclopyr; tricyclazole; tricyclohexyltin; hydroxide; tridemorph; tridiphane; trietazine; trifenofos; trifloxystrobin; trifloxysulfuron; triflumizole; triflumuron; trifluralin; triflusulfuron; trifop; trifopsime; triforine; trimeturon; triphenyltin; triprene; tripropindan; tritac; triticonazole; tritosulfuron; uniconazole; uniconazole-P; validamycin; vamidothion; vaniliprole; vernolate; vinclozolin; XMC; xylachlor; xylenols; xylylcarb; zarilamid; zeta-cypermethrin; zinc naphthenate; zineb; zolaprofos; zoxamide trichlorophenate; 1,2-dichloropropane; 1,3-dichloropropene; 2-methoxyethylmercury chloride; 2-phenylphenol; 2,3,3-TPA; 2,3,6-TBA; 2,4-D; 2,4-DB; 2,4-DEB; 2,4-DEP; 2,4-DP; 2,4-MCPB; 2,4,5-T; 2,4,5-TB; 2,4,5-TP; 3,4-DA; 3,4-DB; 3,4-DP; 4-CPA; 4-CPB; 4-CPP; 8-hydroxyquinoline sulfate.

Naturally, the crop protection agents b) may also exist as a mixture in the customary mixing ratios. The amount of crop protectant b) is usually 1 to 25% by weight, preferably 3 to 15% by weight, based on the amount of component a).

The crop protection agent b) need not be present as a readymix together with components a) and, if appropriate, c), but may also be admixed before application of components a), and, if appropriate, c), for example as what is known as a tank mix.

Preferred crop protection agents b) are soil-acting agents such as acetochlor, alachlor, aldicarb, asulam, atrazine, benalaxyl, bendiocarb, benfuracarb, benomyl, benthiocarb, borax, bromacil, butachlor, butam, cadusafos, calcium cyanamide, captafol, captan, carbaryl, carbendazim, carbofuran, carbon disulfide, carbon tetrachloride, carbosulfan, carboxin, CDAA, CDEA, CDEC, CEPC, chlor-IPC, chloramben, chlorbromuron, chlordane, chlorfluazuron, chloridazon, chloropicrin, chlorothalonil, chlorotoluron, chloroxifenidim (=chloroxuron), chlorpropham, copper acetate, copper acetoarsenite, copper arsenate, copper carbonate, basic, copper hydroxide, copper naphthenate, copper oleate, copper oxychloride, copper 8-quinolinolate, copper silicate, copper sulfate, copper sulfate, basic, copper zinc chromate, cyanazine, dalapon, dazomet, decarbofuran, di-allate (=diallate), diazinon, dibrom, 1,2-dibromoethane, dichlobenil, 1,2-dichloroethane, dichloromethane, 1,2-dichloropropane, 1,3-dichloroporpene, dieldrin, diphenamid, dipterex, diuron, endosulfan, endrin, epoxiconazole, EPTC, ethalfluralin, ethylan (=ethyl-DDD), ethylene dibromide, ethylene dichloride, ethylene oxide, ethylmercury bromide, ethylmercury chloride, ethylmercury phosphate, fenuron, ferbam, ferrous sulfate, fluchloralin, folpel (=folpet), formaldehyde, fosthiazate, furmecyclox, gamma-BHC, gamma-cyhalothrin, gamma-HCH, guanoctine (=guazatine), HCH, gamma-HCH, heptachlor, hexachlor, hydrogencyanide, imazalil, imazamox, imazapic, imazapyr, imazaquin, imazethapyr, imazosulfuron, imidacloprid, IPC, iprodione, isonoruron, isoprocarb, isoproturon, isouron, lactofen, lenacil, lime sulfur, lindane, linuron, mancopper, mancozeb, maneb, mercuricchloride, mercuric oxide, mercurous chloride, metalaxyl, metalaxyl-M, metam, metazachlor, methabenzthiazuron, metham, methyl bromide, methylchloroform, isothiocyanate, methyl-mercaptophos, methylmercaptophos, methylmercury benzoate, methylmercury, metiram, metobenzuron, metobromuron, metolachlor, S-metolachlor, metosulam, metoxuron, metribuzin, mirex, molinate, monalide, monolinuron, monuron, MSMA, nabam, naled, naphthalic anhydride, napropamide, naptalam, neburea, neburon, nitralin, norflurazon, noruron, novaluron, ofurace, oryzalin, oxadixyl, oxine-copper, oxine-Cu, oxycarboxin, PCNB, PCP, pebulate, pendimethalin, phenylmercuriurea, phenylmercury acetate, phenylmercury chloride, phenylmercury nitrate, phenylmercury salicylate, phorate, phosphocarb, phthalide, phthalophos, phthalthrin, pichloram, pirimicarb, potassium arsenite, potassium cyanate, potassium polysulfide, potassium thiocyanate, prochloraz, procymidone, profluralin, propham, propiconazole, propineb, prosulfalin, pyrazon, quinclorac, sevin, siduron, simazine, sulfur, sulfuric acid, tebuconazole, terbacil, terraclor, thiabendazole, thiacloprid, thiameturon, thiobencarb, thiocarboxime, thiodan, thiodicarb, thiofanocarb, thiophanate, thiophanate-ethyl, thiophanate-methyl, thiram, thiuram, tiabendazole, TMTD, toxaphene, tri-allate, triadimefon, triadimenol, triallate, tribenuron, hydroxide, triflumuron, trifluralin, vernolate, vinclozolin, zineb, 1,2-dichloropropane, 1,3-dichloropropene.

However, the composition according to the invention preferably only comprises components a) and, if appropriate, c).

Further components c) of the mixture M which are suitable are water in minor amounts, for example 1 to 6% by weight based on component a), fillers, water softeners, and the auxiliaries conventionally used in the agricultural sector in customary amounts, for example plant nutrients in various forms, and furthermore fillers such as kaolin clay, bentonite, talc, calcium carbonate; anticaking agents such as finely divided silicas; soluble salts such as sodium chloride, sodium sulfate, ammonium sulfate; surfactants such as alkyl sulfates, alkylsulfonates, alkyl polyglycosides, alkyl ether sulfates, alkylbenzenesulfonates, alkylsulfosuccinates, alkyl esters of mono/diphosphoric acid, sarcosinates, taurates, alkoxylated animal/vegetable fats and oils, glycerol esters, alkoxylated fatty alcohols and oxo alcohols, alkoxylated fatty acids, alkylphenyl ethoxylates, fatty amine alkoxylates, fatty acid amide alkoxylates, sugar surfactants such as sorbitan fatty acid esters and their ethoxylates, ethylene oxide/propylene oxide block polymers; and antifoams, such as silicone surfactants.

The mixture M according to the invention can be used or applied in practice in dry form, for example pure, or as a formulation or else in a liquid medium.

Suitable liquid media are aqueous salt solutions, aqueous nutrient solutions (for example consisting of nutrient salts and/or ureas), in particular water.

As a rule, the mixture M according to the invention is employed in an aqueous medium, in particular water, in a concentration range of from 0.0001 to 6% by weight, preferably 0.001 to 0.01% by weight, in particular 0.0015 to 0.005% by weight, based on the total of mixture M according to the invention and medium.

The mixtures M according to the invention can be marketed as different types of formulations. Suitable types of formulation are liquid suspension concentrates, solid water-dispersible powders, water-dispersible granules and granules for spreading. Water-dispersible granules are preferred.

The total application rate of the mixtures M according to the invention is to be calculated in such a way that a fungicidal, nematicidal or insecticidal effect is observed, which can be determined with a few preliminary experiments. The total application rate is normally in the range of from 0.5 to 50 kg/(hectare, crop, season).

The method according to the invention can be applied to all soils and/or substrates (growth media, for example rockwool) on which useful plants and/or ornamentals are conventionally produced; neutral to basic soils and/or substrates, including volcanic soils, are preferred. Neutral to basic soils and/or substrates are to be understood for the present application as those whose pH is in the range of from 6.2 to 9.0, preferably 7.0 to 8.2.

The method according to the invention can be carried out with all customary irrigation systems or irrigation methods which are described, inter alia, in Antinio L. Alarcon, "tecnologia para cultivos de alto rendimiento" [Technology for high-yielding cultivars], published by: NOVEDADES AGRICOLAS S. A. Torre Pacheco (Murcia), 2000 (ISBN: 84-607-1212-5) or in Yaron, B; Danfors, E. and Vaadia,Y.: Arid zone irrigation (1973, Springer Verlag; chapter "Irrigation Technology", pp. 303–353, for example overhead irrigation, channel irrigation, flooding, pivot irrigation; however, those irrigation systems or irrigation methods which ensure irrigation of the soil or substrate within the drip zone of the plants' foliage, such as trickle irrigation or microsprinkler irrigation, both of which are known, are preferred.

A particular advantage of the mixture M according to the invention is that it is readily dispersible (suspendable) in, for example, water, that is to say that the mixture according to the invention will not settle in the aqueous dispersion (suspension) and/or separate out for example on the surface ("creaming") within foreseeable periods. A good measure for this dispersibility (suspendability) is what is known as the suspension stability as specified in CIPAC MT 168 (CIPAC Handbook F—Page 427—Determination of Suspension Stability of Waterdispersible Granules). Usually, the suspension stability of the aqueous dispersions (suspensions) which comprise the mixture M according to the invention is 50 to 100%, preferably 70 to 100%.

Suitable useful plants are arable crops such as cotton or cereals, but preferably fruit and vegetable crops, preferably perennial crops. Suitable ornamentals are pot plants and cut flowers, preferably perennial crops, such as roses. Examples of fruit and vegetable crops are: tomatoes, capsicums, cucumbers, citrus fruit, bananas, peaches, dessert grapes, apples, pears, olives, mangoes, pawpaws, avocados, strawberries or kiwi fruit.

The present method is distinguished in particular by the fact that the soil is disinfested effectively without toxicological or ecological undesired side effects. The mixture M according to the invention can be employed readily in irrigation systems, in particular for trickle irrigation. Owing inter alia to the fact that the ultrafinely-particular mixture M according to the invention is thoroughly dispersed/suspended in the aqueous medium, this medium can be pumped readily and does not lead to blockage of the irrigation pipeline system or its nozzles or valves, as is the case for example in the case of coarsely particulate suspended solids.

EXAMPLE

In a 2.5 m$^3$ stirred vessel, 730 l/h of a 53% aqueous potassium lignosulfonate solution and 1000 l/h liquid sulfur are mixed, with stirring, and comminuted further using a toothed-disk emulsifier (5 Herz). The mixture is subsequently spray-dried. The solid mixture is mixed with 0.3% anticaking agent. The brown product contains 75% by weight sulfur, 21.5% by weight potassium lignosulfonate, 0.3% by weight anticaking agent and 3.2% by weight of residual water.

The dispersibility amounts to 93%, the 1% suspendibility to 87%. Wet screening residue: 0.05%>75 μm. pH 1%: 8.5. Primary particle size 50%: 3 μm, loose bulk density 0.845, dust number: 5.

We claim:

1. A chemical soil disinfestation method comprising:
    applying a fungicidally, insecticidally or nematicidally active amount of a mixture M comprising a component a) of
    a1) 20 to 96% by weight of sulfur,
    a2) 4 to 80% by weight of a complexing agent selected from the group consisting of:
    nonpolymeric complexing compounds:
        EDTA (ethylenediaminetetraacetic acid), NTA (nitrilotriacetic acid), EDDHA (ethylenediaminedi(orthohydorxyphenyl) acetic acid), DTPA (diethylenetriaminepentaacetic acid), HEDTA (hydorxyethylenediaminetriacetic acid), and
    polymeric complexing agents:
        polyacrylic acid and its salts, polymethacrylic acid and its salts, polymaleic acid and its salts, polyvinylpyrrolidone, copolymers of acrylic acid and maleic acid, copolymers of vinylpyrrolidone and vinyl acetate, graft copolymers of vinylpyrrolidone and C20 α-olefin, copolymers of vinylpyrrolidone and acrylic acid, copolymers of vinylpyrrolidone and dimethylaminoethyl acrylate, copolymers of methyl vinyyl ether and maleic anhydride (derivatives), copolymers of styrene and maleic anhydride, polyaspartic acid and its salts, poly-p-vinylbenzenesulfonic acid and its salts, copolymers of ethylene and/or propylene and/or isobutene and (meth)acrylic acid, modified starches, modified celluloses, alginates, liginin derivatives, chitosans, modified polysaccharides, phenolsulfonic acid formaldehyde condensates, naphthalenesulfonic acid formaldehyde condensates and,
    optionally, at least one crop protection agent b), and,
    optionally, at least one component c),
    to a growth substrate to be disinfested.

2. The method as claimed in claim 1, wherein a2) comprises a polymeric sequestrant.

3. The method as claimed in claim 1, wherein a2) comprises at least one of a lignosulfonate, a naphthalenesulfonic acid/formaldehyde condensate, and a mixture of lignosulfonate and naphthalenesulfonic acid/formaldehyde condensate.

4. The method as claimed in claim 1, wherein a2) comprises at least one of an alkali metal lignosulfonate and an alkaline earth metal lignosulfonate.

5. The method as claimed in claim 1, wherein the mixture M is flowable and has a mean particle size of from 50 μm to 4 mm.

6. The use of mixture M as defined in claim 1 as chemical soil disinfestation composition.

7. The method of claim 1 wherein mixture M is applied to soil proximate the roots of a plant.

8. The method of claim 7 wherein mixture M is applied to said soil using an irrigation system.

9. The method of claim 1 wherein mixture M is applied to said growth substrate using an irrigation system.

* * * * *